(12) United States Patent
Martin et al.

(10) Patent No.: US 8,108,173 B2
(45) Date of Patent: Jan. 31, 2012

(54) COMPENSATING FOR SYSTEM DELAY AND/OR EXTRANEOUS ILLUMINATION IN ANALYTE ANALYZATION

(75) Inventors: Jesus D. Martin, Wallingford, CT (US); John R. DelFavero, East Hampton, CT (US)

(73) Assignee: RIC Investments, LLC, Wilmington, DE (US)

( * ) Notice: Subject to any disclaimer, the term of this patent is extended or adjusted under 35 U.S.C. 154(b) by 705 days.

(21) Appl. No.: 12/194,112

(22) Filed: Aug. 19, 2008

(65) Prior Publication Data
US 2010/0318309 A1    Dec. 16, 2010

Related U.S. Application Data

(60) Provisional application No. 60/957,262, filed on Aug. 22, 2007.

(51) Int. Cl.
*G06F 19/00* (2011.01)
(52) U.S. Cl. ...................................................... 702/106
(58) Field of Classification Search .................. 702/106
See application file for complete search history.

(56) References Cited

U.S. PATENT DOCUMENTS

| 6,616,896 B2 | 9/2003 | Labuda et al. |
| 6,632,402 B2 | 10/2003 | Blazewicz et al. |

OTHER PUBLICATIONS

Gruzinskii, Spectral-Luminescent Properties That Determine the Generation Capacities and Features of Phthalimides, Translated from Zhurnal Prikladnoi Spektroskopii, vol. 29, No. 4, pp. 614-620, Oct. 1978. Original article submitted Jul. 23, 1976, @1979, Plenum Publishing Corporation p. 1179-1184.*

* cited by examiner

*Primary Examiner* — Tung S Lau

(57) ABSTRACT

A sensor that determines information related to a gaseous analyte in a body of fluid. The sensor comprises an emitter, a luminescable medium, a radiation sensor, and a processor. The emitter emits electromagnetic radiation having an oscillating intensity. The luminescable medium communicates with the body of fluid and emits luminescent radiation in response to the received electromagnetic radiation. The radiation sensor receives the luminescent radiation, and generates an output signal based on the intensity of the received luminescent radiation. The processor samples the output signal generated by the radiation sensor at two or more predetermined periodic points over the oscillation of the intensity of the electromagnetic radiation to determine information from the samples related to a phase difference between the oscillation of the intensity of the electromagnetic radiation emitted by the emitter and oscillation of the intensity of the luminescent radiation received by the radiation sensor.

6 Claims, 4 Drawing Sheets

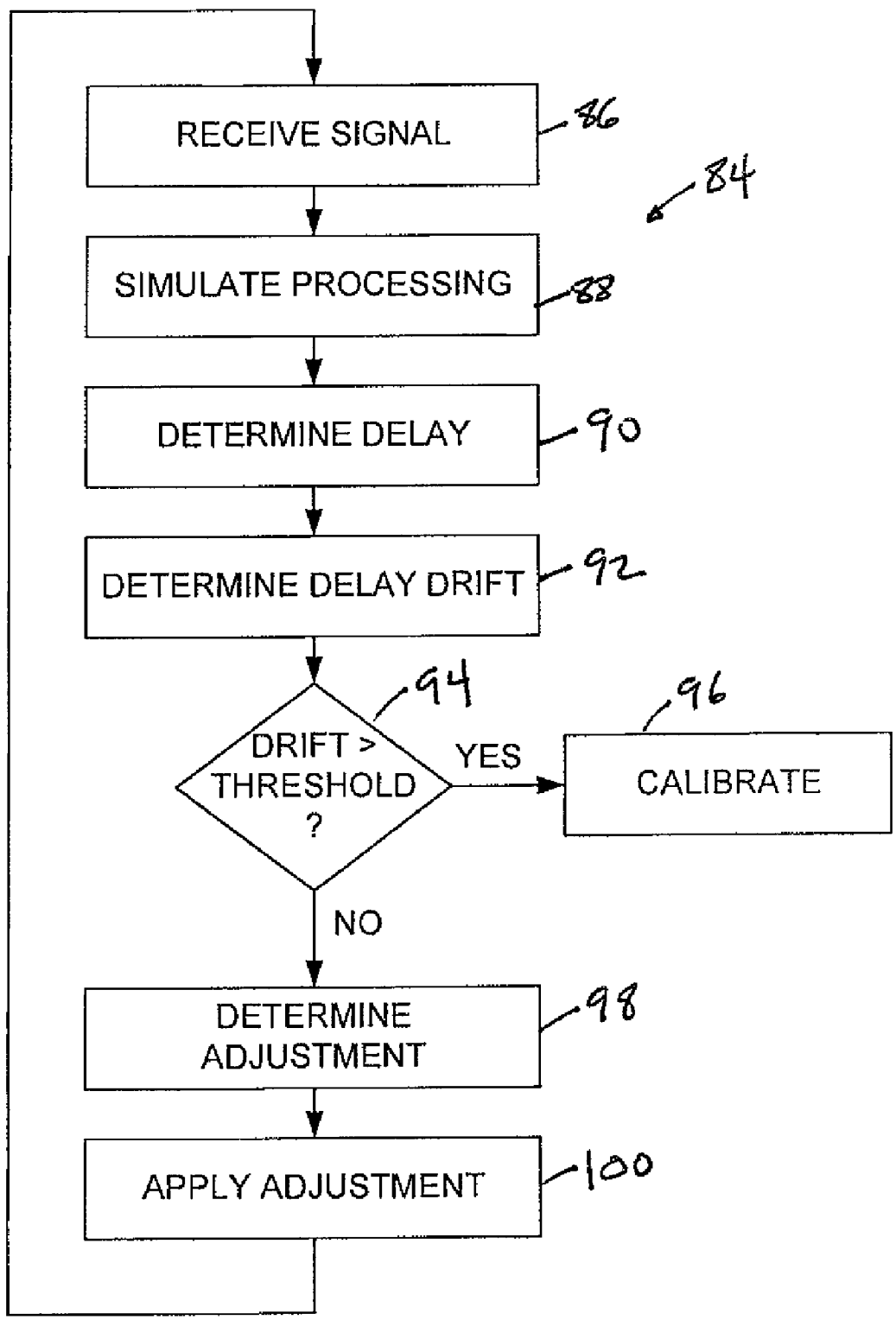

COMPENSATING FOR SYSTEM DELAY AND/OR EXTRANEOUS ILLUMINATION IN ANALYTE ANALYZATION

CROSS-REFERENCE TO RELATED APPLICATIONS

This application claims priority under 35 U.S.C. §119(e) from provisional U.S. patent application No. 60/957,262, filed Aug. 22, 2007, the contents of which are incorporated herein by reference.

BACKGROUND OF THE INVENTION

1. Field of the Invention

The invention relates generally to a system and method that determines information related to one or more gaseous analytes in a body of fluid, and, more particularly, to adjusting for inaccuracies in the determination of such information.

2. Description of the Related Art

The use of luminescence-quenching detection to determine information related to gaseous analytes present in a body of gas is known. However, conventional systems may not adequately compensate for certain systematic errors introduced by the components of these systems. For example, photosensitive detectors generally used to detect a return signal from a luminescable medium may introduce system delays that are not adequately compensated for in conventional systems. This may lead to inaccurate and/or imprecise determinations of information related to the gaseous analytes. Other examples of sources of inaccuracy and/or imprecision also exist (e.g., delays associated with signal processing, inadequate optical filtering, cross-talk, etc.).

SUMMARY OF THE INVENTION

One aspect of the invention relates to a sensor configured to determine information related to one or more gaseous analytes in a body of fluid. In one embodiment, the sensor comprises an emitter, a luminescable medium, a radiation sensor, and a processor. The emitter is configured to emit electromagnetic radiation such that the intensity of the emitted electromagnetic radiation oscillates in a periodic manner. The luminescable medium is in operative communication with the body of fluid and is arranged to receive electromagnetic radiation from the emitter. The luminescable medium emits luminescent radiation in response to the electromagnetic radiation it receives from the emitter. The radiation sensor is arranged to receive the luminescent radiation, and generates an output signal that conveys information related to the intensity of the received luminescent radiation. The processor is configured to sample the output signal generated by the radiation sensor at two or more predetermined periodic points over the oscillation of the intensity of the electromagnetic radiation emitted by the emitter, and to determine information, based on the samples of the output signal, related to a phase difference between the oscillation of the intensity of the electromagnetic radiation emitted by the emitter and oscillation of the intensity of the luminescent radiation received by the radiation sensor.

Another aspect of the invention relates to a method of determining information related to one or more gaseous analytes in a body of fluid. In one embodiment, the method comprises emitting electromagnetic radiation having an intensity that oscillates in a periodic manner, the electromagnetic radiation being emitted such that the emitted electromagnetic radiation becomes incident on a luminescable medium in operative communication with the body of fluid, wherein the luminescable medium emits luminescent radiation in response to the electromagnetic radiation it receives from the emitter; receiving at least a portion of the luminescent radiation; generating an output signal that conveys information related to the intensity of the received luminescent radiation; sampling the output signal at two or more predetermined periodic points over the oscillation of the intensity of the emitted electromagnetic radiation; and determining information, based on the samples of the output signal, related to a phase difference between the oscillation of the intensity of the emitted electromagnetic radiation and oscillation of the intensity of the received luminescent radiation.

Another aspect of the invention relates to a sensor configured to determine information related to one or more gaseous analytes in a body of fluid. In one embodiment, the sensor comprises means for emitting electromagnetic radiation having an intensity that oscillates in a periodic manner, the electromagnetic radiation being emitted such that the emitted electromagnetic radiation becomes incident on a luminescable medium in operative communication with the body of fluid, wherein the luminescable medium emits luminescent radiation in response to the electromagnetic radiation it receives from the emitter; means for receiving at least a portion of the luminescent radiation; means for generating an output signal that conveys information related to the intensity of the received luminescent radiation; means for sampling the output signal at two or more predetermined periodic points over the oscillation of the intensity of the emitted electromagnetic radiation; and means for determining information, based on the samples of the output signal, related to a phase difference between the oscillation of the intensity of the emitted electromagnetic radiation and oscillation of the intensity of the received luminescent radiation.

Another aspect of the invention relates to a sensor configured to determine information related to one or more gaseous analytes in a body of fluid. In one embodiment, the sensor comprises an emitter, a luminescable medium, a radiation sensor, and a processor. The emitter is configured to emit electromagnetic radiation such that the intensity of the emitted electromagnetic radiation oscillates in a periodic manner. The luminescable medium is in operative communication with the body of fluid, and is arranged to receive electromagnetic radiation from the emitter. The luminescable medium emits luminescent radiation in response to the electromagnetic radiation it receives from the emitter. The radiation sensor is arranged to receive the luminescent radiation, and to generates an output signal that conveys information related to the intensity of the received luminescent radiation. The processor is configured to determine a first phase difference between the oscillation of the intensity of the electromagnetic radiation emitted by the emitter and oscillation of the output signal generated by the radiation sensor, to determine information related to an amplitude of the oscillation of the output signal generated by the radiation sensor, and to determine a second phase difference between the oscillation of the intensity of the electromagnetic radiation emitted by the emitter and oscillation of the intensity of the luminescent radiation received by the radiation sensor according to a function that varies with both of the first phase difference and the amplitude of the oscillation of the output signal generated by the radiation sensor.

Another aspect of the invention relates to a method of determining information related to one or more gaseous analytes in a body of fluid. In one embodiment, the method comprises emitting electromagnetic radiation having an intensity that oscillates in a periodic manner, the electromagnetic radiation being emitted such that the emitted electromagnetic radiation becomes incident on a luminescable medium in operative communication with the body of fluid, wherein the luminescable medium emits luminescent radiation in response to the electromagnetic radiation it receives from the emitter; receiving at least a portion of the luminescent radiation; generating an output signal that conveys information related to the intensity of the received luminescent radiation; determining a first phase difference between the oscillation of the intensity of the emitted electromagnetic radiation and oscillation of the generated output signal; determining information related to an amplitude of the oscillation of the generated output signal; and determining a second phase difference between the oscillation of the intensity of the emitted electromagnetic radiation and oscillation of the intensity of the received luminescent radiation according to a function that varies with both of the first phase difference and the amplitude of the oscillation of the generated output signal.

Another aspect of the invention relates to a sensor of determining information related to one or more gaseous analytes in a body of fluid. In one embodiment, the sensor comprises means for emitting electromagnetic radiation having an intensity that oscillates in a periodic manner, the electromagnetic radiation being emitted such that the emitted electromagnetic radiation becomes incident on a luminescable medium in operative communication with the body of fluid, wherein the luminescable medium emits luminescent radiation in response to the electromagnetic radiation it receives from the emitter; means for receiving at least a portion of the luminescent radiation; means for generating an output signal that conveys information related to the intensity of the received luminescent radiation; means for determining a first phase difference between the oscillation of the intensity of the emitted electromagnetic radiation and oscillation of the generated output signal; means for determining information related to an amplitude of the oscillation of the generated output signal; and means for determining a second phase difference between the oscillation of the intensity of the emitted electromagnetic radiation and oscillation of the intensity of the received luminescent radiation according to a function that varies with both of the first phase difference and the amplitude of the oscillation of the generated output signal.

Another aspect of the invention relates to a sensor configured to determine information related to one or more gaseous analytes in a body of fluid. In one embodiment, the sensor comprises an emitter, a driving module, a luminescable medium, a radiation sensor, and a processor. The emitter is configured to emit electromagnetic radiation such that the intensity of the emitted electromagnetic radiation oscillates in a periodic manner. The driving module is configured to generate a driving signal that is transmitted to the emitter, wherein one or more aspects of the driving signal oscillates in a manner that produces the oscillation of the intensity of the electromagnetic radiation emitted by the emitter. The luminescable medium is in operative communication with the body of fluid and is arranged to receive electromagnetic radiation from the emitter. The luminescable medium emits luminescent radiation in response to the electromagnetic radiation it receives from the emitter. The radiation sensor is arranged to receive the luminescent radiation, and to generate an output signal that conveys information related to the intensity of the received luminescent radiation. The processor comprises a first processing module and a second processing module. The first processing module is configured to process the output signal generated by the radiation sensor to determine information related to a phase difference between the oscillation of the intensity of the electromagnetic radiation emitted by the emitter and oscillation of the intensity of the luminescent radiation received by the radiation sensor. The second processing module is configured to receive a signal that corresponds to the driving signal generated by the driving module, to apply one or more processing procedures to the received signal that simulate one or more of the processing procedures applied by the first processing module to the output signal generated by the radiation sensor, and to determine a present estimate of a delay caused by the first processing module in processing the output signal generated by the radiation sensor based on a comparison of the received signal without processing by the second processing module and the received signal subsequent to processing by the second processing module.

Another aspect of the invention relates to a method of determining information related to one or more gaseous analytes in a body of fluid. In one embodiment, the method comprises generating an oscillating driving signal; transmitting the driving signal to an emitter configured to emit electromagnetic radiation onto a luminescable medium in operative communication with the body of fluid, the luminescable medium emitting luminescent radiation in response to the electromagnetic radiation it receives from the emitter, wherein the driving signal causes the intensity of the electromagnetic radiation emitted by the emitter to oscillate in a periodic manner; receiving the luminescent radiation; generating an output signal that conveys information related to the intensity of the received luminescent radiation; processing the generated output signal to determine information related to a phase difference between the oscillation of the intensity of the emitted electromagnetic radiation and oscillation of the intensity of the received luminescent radiation; receiving a signal that corresponds to the oscillating driving signal; applying one or more processing procedures to the received signal that simulate one or more of the processing procedures applied to the generated output signal in determining information related to the phase difference; and determining a present estimate of a delay associated with processing the generated output signal based on a comparison of the received signal without processing and the received signal subsequent to the application of the one or more processing procedures.

Another aspect of the invention relates to a sensor configured to determine information related to one or more gaseous analytes in a body of fluid. In one embodiment, the sensor comprises means for generating an oscillating driving signal; means for transmitting the driving signal to an emitter configured to emit electromagnetic radiation onto a luminescable medium in operative communication with the body of fluid, the luminescable medium emitting luminescent radiation in response to the electromagnetic radiation it receives from the emitter, wherein the driving signal causes the intensity of the electromagnetic radiation emitted by the emitter to oscillate in a periodic manner; means for receiving the luminescent radiation; means for generating an output signal that conveys information related to the intensity of the received luminescent radiation; means for processing the generated output signal to determine information related to a phase difference between the oscillation of the intensity of the emitted electromagnetic radiation and oscillation of the intensity of the received luminescent radiation; means for receiving a signal that corresponds to the oscillating driving signal; means for applying one or more processing procedures to the received signal that simulate one or more of the processing procedures applied to the generated output signal in determining information related to the phase difference; and means for determining a present estimate of a delay associated with means for processing the generated output signal based on a comparison of the received signal without processing and the received signal subsequent to the application of the one or more processing procedures.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which faun a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 4 illustrates a method of adjusting a determination of a processing delay provided to a signal by a processor.

DETAILED DESCRIPTION OF THE EXEMPLARY EMBODIMENTS

Figure 1:
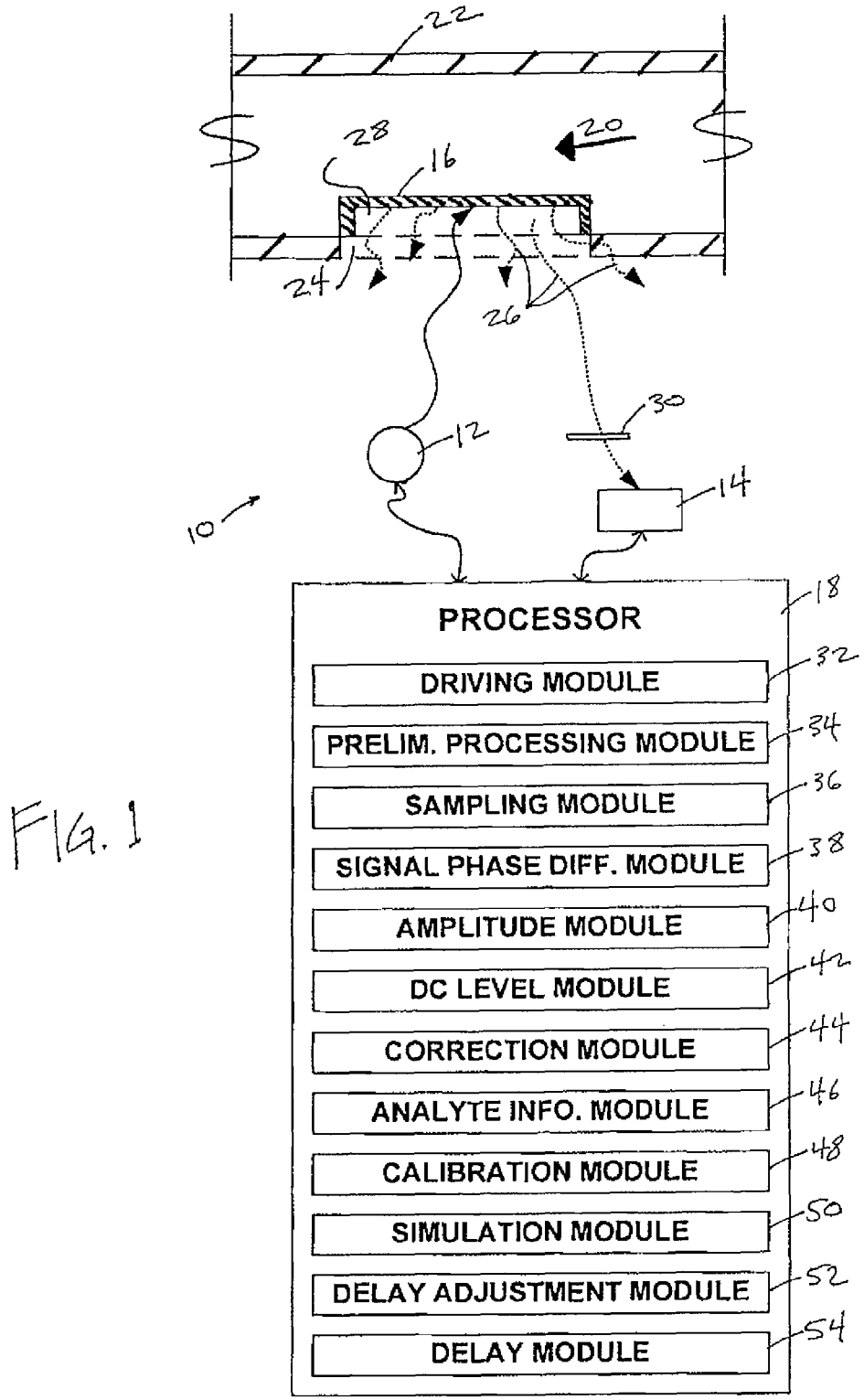
FIG. 1 is a schematic illustration of a system configured to determine information related to one or more gaseous analytes in a body of gas, according to one embodiment of the invention.

FIG. 1 is a schematic illustration of a system 10 configured to determine information related to one or more analytes in a body of fluid. System 10 includes one or more emitters 12, a photosensitive detector 14, a luminescable medium 16, and a processor 18. System 10 may determine information related to one or more gaseous analytes in the body of fluid (e.g., a body of gas) contained within a flow path 20. In one example, flow path 20 is defined by a conduit 22 adapted to carry gas to and/or from a patient. In a more particular example, conduit 22 may cooperate with a patient interface appliance configured to communicate with an airway of the patient. Some examples of the patient interface appliance may include, for example, an endotracheal tube, a nasal canula, a tracheotomy tube, a mask, or other patient interface appliances. The present invention is not limited to these examples, and contemplates determination of analytes in a body of fluids in a wide variety of contexts. For instance, a system similar to the one illustrated in system 10 may be implemented in a bioreactor, or other system, to determine information related to one or more gaseous analytes in body of fluid that includes gas and/or liquid.

In some implementations, emitter 12, photosensitive detector 14, and/or luminescable medium 16 define a sensor. The sensor may be formed as a single unit for integration into an airway adapter. For example, U.S. Pat. No. 6,616,896 to Labuda et al., entitled "OXYGEN MONITORING APPARATUS," and issued Sep. 9, 2003 ("the '896 patent"), and U.S. Pat. No. 6,632,402 to Blazewicz et al., entitled "OXYGEN MONITORING APPARATUS," and issued Oct. 14, 2003 ("the '402 patent") both describe sensors that (1) include components similar to some or all of emitter 12, photosensitive detector 14, and/or luminescable medium 16, and (2) determine information related to one or more analytes in a body of gas. Both of the '896 and '402 patents are hereby incorporated, in their entireties, into this disclosure by reference.

Emitter 12 emits electromagnetic radiation that is directed onto luminescable medium 16. As will be discussed further below, the electromagnetic radiation emitted by emitter 12 includes electromagnetic radiation with a wavelength that causes luminescable medium 16 to luminescence. Emitter 12 may include one or more Organic Light Emitting Diodes ("OLEDs"), lasers (e.g., diode lasers or other laser sources), Light Emitting Diodes ("LEDs"), Hot Cathode Fluorescent Lamps ("HCFLs"), Cold Cathode Fluorescent Lamps ("CCFLs"), incandescent lamps, halogen bulbs, received ambient light, and/or other electromagnetic radiation sources.

In one implementation, emitter 12 includes one or more green and/or blue LEDs. These LEDs typically have high intensity in the luminescable composition absorption region of luminescable medium 16 and output smaller amounts of radiation at other wavelengths (e.g., UV and/or near-UV). This minimizes stray interfering light and photo degradation of the sensor formed by emitter 12, photosensitive detector 14, and/or luminescable medium 16.

While, as described above, the present invention is by no means limited to the use of LEDs, other advantages of implementing LEDs as emitter 12 include their light weight, compactness, low power consumption, low voltage requirements, low heat production, reliability, ruggedness, relatively low cost, and stability. Also they can be switched on and off very quickly, reliably, and reproducibly.

In some implementations, system 10 may include one or more optical elements (not shown) to guide, focus, and/or otherwise process radiation emitted by emitter 12. For example, one or more lenses may collimate the radiation in a selected direction. As more particular examples, both of the incorporated '896 and '402 patents disclose the use of optical elements that process radiation emitted by an emitter similar to emitter 12.

The electromagnetic radiation from emitter 12 may arrive at luminescable medium 16 with a predetermined amplitude modulation (e.g., having a predetermined frequency, having a predetermined maximum and/or minimum amplitude, etc.). The predetermined amplitude modulation is periodic. As used herein, periodic modulation refers to any modulation of amplitude wherein the frequency and/or period of the modulation is predetermined. This encompasses embodiments in which the frequency and/or period are not constant, and/or embodiments in which the emission of the electromagnetic radiation is not continuous (e.g., pulsed). In one embodiment, emitter 12 may be driven to emit the electromagnetic radiation with the predetermined amplitude modulation. In another embodiment, system 10 may include one or more optical elements (not shown) that modulate the amplitude of electromagnetic radiation emitted by emitter 12. The one or more optical elements may include one or more periodically driven active elements (e.g., a liquid crystal stack, etc.) and/or one or more passive elements that are periodically moved into and out of an optical path of the electromagnetic radiation emitted by emitter 12 (e.g., filters, half-mirrors, etc.).

As can be seen in FIG. 1, conduit 22 may include a window 24. Window 24 may be substantially transparent to enable electromagnetic radiation, such as the electromagnetic radiation emitted by emitter 12, to enter and/or exit the interior of conduit 22. For instance, window 24 may be formed of sapphire, one or more polymers (e.g., polyethelyne, etc.), a glass, and/or other substantially transparent materials. In some embodiments (not shown), conduit 22 may include two windows similar to window 24. As is shown and described in the '402 reference, the two windows may be disposed in conduit 22 opposite from each other to enable electromagnetic radiation to pass through conduit 22. In this embodiment, photosensitive detector 14 may be positioned on an opposite side of conduit 22 from emitter 12.

Luminescable medium 16 is a medium that, in response to radiation from emitter 12 and/or some other excitation energy, luminesces to emit luminescent electromagnetic radiation, indicated by wavy lines 26, in a substantially omni-directional manner at a wavelength different from that of the electromagnetic radiation provided by emitter 12 (e.g., luminescent radiation 26 may be within the red portion of the wavelength spectrum). The intensity and/or persistence of this luminesced electromagnetic radiation 26 rises and falls according to the relative amounts of one or more analytes included in the body of gas within conduit 22. In one embodiment, oxygen causes a modification of the intensity and/or persistence of luminescent radiation 26 by quenching the luminescence reaction. As the concentration of oxygen increases, the modification of the intensity and/or persistence of luminescent radiation 26 will decrease. In one embodiment, luminescable medium 16 is formed as a luminescent film. For example, both of the incorporated '896 and '402 patents disclose films that may be employed as luminescable medium 16.

In the embodiment illustrated in FIG. 1, luminescable medium 16 is disposed on a transparent thermal capacitor 28. Thermal capacitor 28 is employed to maintain luminescable medium 16 at a substantially constant operating temperature and thereby reduce or eliminate inaccuracies in system 10 attributable to variations in the temperature of luminescable medium 16. Thermal capacitor 28 is transparent in order to enable electromagnetic radiation emitted from emitter 12 to reach luminescable medium 16, and for luminescent radiation 26 to travel back through thermal capacitor 28 toward detector 14.

Photosensitive detector 14 is configured such that it is positioned to receive at least a portion of luminesced electromagnetic radiation 26 from luminescable medium 16. Based on the received radiation, photosensitive detector 14 generates one or more output signals related to one or more properties of the received radiation. For example, the one or more output signals may be related to an amount of the radiation, an intensity of the radiation, a modulation of the radiation, and/or other properties of the radiation. In one embodiment, photosensitive detector 14 includes a PIN diode. In other embodiments, other photosensitive devices are employed as photosensitive detector 14. For instance, photosensitive detector 14 may take the form of a diode array, a CCD chip, a CMOS chip, and/or other photosensitive devices.

System 10 is configured such that the one or more output signals generated by photosensitive detector 14 are related to one or more properties of received radiation primarily within a wavelength range that contains the wavelength of the luminescent radiation 26, but does not include electromagnetic radiation of other wavelengths. For example, in one embodiment, a filter (or filters) 30 may be disposed proximate to photosensitive detector 14 that reduces the amount of electromagnetic radiation not of the same wavelength as luminescent radiation 26 that becomes incident on photosensitive detector 14 (e.g., filter 30 is a filter that transmits substantially only radiation in the red portion of the wavelength spectrum). In one embodiment, photosensitive detector 14 comprises a wavelength sensitive photodiode ("WSPD") that is especially responsive in the generation of the one or more output signals to electromagnetic radiation with a wavelength that corresponds to the wavelength of luminescent radiation 26.

Despite design features that reduce the amount of electromagnetic radiation other than luminescent radiation 26 that is reflected in the one or more output signals generated by photosensitive detector 14 (e.g., filter 30, the implementation of a WSPD as detector 14, etc.), such features may not completely exclude electromagnetic radiation emanating from sources other than luminescable medium 16 from influencing the output signal(s). For example, ambient illumination, electromagnetic radiation emitted from emitter 12 and reflected by a component of system 10 (e.g., window 24, capacitor 26, conduit 22, etc.), and/or other electromagnetic radiation may influence the output signal(s) generated by photosensitive detector 14. Such radiation creates two inaccuracies in the output signal(s) generated by photosensitive detector 14 if information is derived based on the output signal(s) assuming that the output signal(s) correspond to only luminescent radiation 26. These two inaccuracies include an inaccuracy in the intensity (e.g., the extraneous radiation increases the intensity reflected in the output signal(s)), and a difference in decay time (e.g., the extraneous radiation caused by reflection of radiation emitted from emitter 12 will have a smaller decay time than luminescent radiation 26). As will be discussed below, these inaccuracies may be accounted for (at least to some extent) in processing the output signal(s) to determine information related to the one or more analytes present in the body of gas.

In one embodiment, one or more gases present in the body of gas at luminescable medium 16 quench the luminescence exhibited by luminescable medium 16 in response to receiving radiation from emitter 12. More particularly, the peak luminescence and decay time of the luminescence exhibited by luminescable medium 16 decreases as the amount of these one or more gases present at luminescable medium 16 increases. In one embodiment, the one or more gases may include oxygen.

Processor 18 is operatively coupled with emitter 12 and photosensitive detector 14. Processor 18 is configured to determine information about one or more analytes in a body of gas within flow path 20. Processor 18 determines this information based on known and/or measured information related to (i) the emission of radiation by emitter 12 onto luminescable medium 16 and (ii) radiation that is received by photosensitive detector 14, including luminescent radiation 26. For example, processor 18 may determine information about one or more analytes in the body of gas based on the relationship between the one or more analytes and the decay time of the luminescence of luminescable medium 16.

As is shown in FIG. 1, in an exemplary embodiment of the present invention, processor 18 includes a driving module 32, a preliminary processing module 34, a sampling module 36, a signal phase difference module 38, a signal amplitude module 40, a DC level module 42, a correction module 44, an analyte information module 46, a calibration module 46, a simulation module 50, processing delay module 52, and a delay adjustment module 54. Modules 32, 34, 36, 38, 40, 42, 44, 46, 48, 50, 52, and 54 may be implemented in software; hardware; firmware; some combination of software, hardware, and/or firmware; and/or otherwise implemented. It should be appreciated that although modules 32, 34, 36, 38, 40, 42, 44, 46, 48, 50, 52, and 54 are illustrated in FIG. 1 as being co-located within a single processing unit, processor 18, however, may include multiple processing units, and that some of these processing units may be located remotely from each other. In such embodiments, one or more of modules 32, 34, 36, 38, 40, 42, 44, 46, 48, 50, 52, and/or 54 may be located remotely from the other modules and operative communication between the modules may be achieved via one or more communication links. Such communication links may be wireless or hard wired.

Driving module 32 is configured to generate a driving signal that is transmitted to emitter 12. The driving signal is generated such that one or more aspects of the driving signal oscillates in a manner that produces the oscillation of the intensity of the electromagnetic radiation emitted by emitter 12. For example, the driving signal may be a power signal, the amplitude of which oscillates. As another example, the driving signal may be a control signal provided to a switch that controls the intensity of the electromagnetic radiation emitted from emitter 12. The oscillation of the one or more aspects of the driving signal is designed such that the oscillation of the electromagnetic radiation emitted by emitter 12 has a predetermined amplitude, frequency, and/or waveform. It should be appreciated that the description above of the driving signal being transmitted to emitter 12 would include transmission of the driving signal to an element associated with emitter 12 to controllably vary the intensity level of the electromagnetic radiation emitted therefrom (e.g., an LCD stack, an actuator that controllably positions filters with respect to emitter 12, etc.). Further, the generation of the driving signal by driving module 32, in one embodiment, includes actually generating the driving signal. In another embodiment, the generation of the driving signal includes controlling the generation of the driving signal. Although driving module 32 is illustrated in FIG. 1 as being integrated within processor 18, this is not intended to limiting. In one embodiment, driving module 32 is separate and distinct from processor 18, and may or may not be in operative communication with processor 18.

Preliminary processing module 34 receives the output signal(s) generated by photosensitive detector 14 and executes one or more preliminary processing procedures on the received output signal(s). In one embodiment, preliminary processing module 34 encodes the output signal(s) (e.g., from analog to digital, from one digital form to another digital form, etc.). In one embodiment, preliminary processing module 34 filters the output signal(s). For example, preliminary processing module 34 may provide an anti-aliasing filter that reduces aliasing in the output signal(s). In processing the output signal(s) generated by photosensitive detector 14, preliminary processing module 34 introduces a delay in the output signal(s). As is discussed below, in one embodiment, this delay is accounted for (at least to some extent) in determining information related to the one or more analytes present in the body of gas.

Sampling module 36 samples the one or more output signals generated by photosensitive detector 14 (e.g., after preliminary processing by preliminary processing module 34). As was mentioned above with respect to driving module 32, in one embodiment, the intensity of electromagnetic radiation emitted by emitter 12 oscillates with a predetermined frequency. The predetermined frequency corresponds to a predetermined period T of oscillation. In one embodiment, sampling module 36 samples the one or more output signals generated by detector 14 substantially at two or more predetermined periodic points over the oscillation of the intensity of the electromagnetic radiation emitted by emitter 12. For illustrative purposes, T is discussed hereafter as being expressed in terms of 360°. However, it should be appreciated that this discussion could just as easily be achieved using radians to describe T.

As used herein, a "periodic point" of a function is a point which returns to itself after a certain number of function iterations or a certain amount of time. For instance, a periodic point of the oscillation of the intensity of the electromagnetic radiation emitted by emitter 12 would include a point in the oscillation that occurs at each oscillation (e.g., 0° in each oscillation, 60° in each oscillation, 90° in each oscillation, etc.).

In one embodiment, sampling module 36 may sample the output signal(s) at predetermined periodic points separated by a predetermined interval. By way of non-limiting example, for reasons discussed below with respect to signal phase difference module 38, in one embodiment, sampling module 36 samples the one or more output signals at predetermined points separated by 90° (e.g., T/4). For instance, the predetermined points may be 0° and 90° with respect to T. The predetermined points, in some instances, may include more than two points (e.g., 0°, 90°, 180°, and/or 270°). In other instances, the predetermined points may be separated by 60° (e.g., T/6). As an example of such instances, the predetermined points may include 0° and 60°.

In one embodiment, sampling module 36 determines the occurrence of the predetermined periodic points in the oscillation of the intensity of the electromagnetic radiation emitted from emitter 12 based on information received from driving module 32. For example, sampling module 36 may receive a signal having one or more aspects that oscillate in concert with the one or more oscillating aspects of the driving signal generated by driving module 32. As another example, sampling module 36 may receive the driving signal itself. As yet another example, sampling module 36 may receive a signal that indicates (e.g., via pulses, etc.) the occurrence of one or more predetermined points in the oscillation of the one or more oscillating aspects of the driving signal (e.g., at 0°). In one embodiment, sampling module 36 determines the occurrence of the predetermined periodic points in the oscillation of the intensity of the electromagnetic radiation emitted from emitter 12 based on a timer included within sampling module 36.

Signal phase difference module 38 determines a phase difference between oscillation of the output signal(s) generated by photosensitive detector 14 (e.g., reflecting, at least in part, oscillation of one or more properties of the luminescent radiation 26 received at detector 14) subsequent to processing by preliminary processing module 34 and the oscillation of electromagnetic radiation emitted by emitter 12. In one embodiment, signal phase difference module 38 determines the phase difference without receiving information related to the oscillation of the intensity of electromagnetic radiation emitted by emitter 12 (e.g., information related to the driving signal discussed above with respect to the information received by sampling module 36). Instead, signal phase difference module 38 determines the phase difference based solely on the samples of the processed output signal(s) that are provided by sampling module 36.

By way of illustration, in one embodiment, an output signal generated by photosensitive detector 14 and processed by preliminary processing module 34 may oscillate sinusoidally (e.g., representing sinusoidal oscillation of the intensity of luminescent radiation 26 incident on photosensitive detector 14), and may be represented as:

$$I(t) = A \sin(\omega t - \theta), \quad (1)$$

where "A" represents the amplitude of the output signal generated by detector 14 and processed by module 34 (which is related to the amplitude of the intensity of luminescent radiation 26), "$\omega$" represents the angular frequency of the oscillation of the intensity of the electromagnetic radiation emitted by emitter 12 (when working in degrees, $\omega$ may be represented as 360°/T), "t" represents time, and "$\theta$" represents the delay in phase (or phase difference) between the signal generated by detector 14 and processed by module 34 and the oscillation of the intensity of the electromagnetic radiation emitted by emitter 12. As mentioned above, in one embodiment, sampling module 36 samples the signal at two predetermined periodic points over the oscillation of the intensity of the electromagnetic radiation emitted by emitter 12.

For example, in one embodiment, samples of the signal are taken by sampling module 36 at ωt=0°, and at ωt=90°. In this embodiment, phase difference module 38 processes these samples to determine information related to θ, such as tan(θ), which can be implemented as a representation of θ, and/or from which θ may be determined with relatively little further processing. As should be appreciated from equation (1), the sample taken by sampling module 36 at ωt=0° may be represented as follows:

$$I_{0°} = A\sin(0-\theta) = -A\sin(\theta), \quad (2)$$

and the sample taken by sampling module 36 at ωt=90° may be represented thusly:

$$I_{90°} = A\sin(90°-\theta) = A\cos(\theta). \quad (3)$$

In one embodiment, by dividing the sample taken at ωt=0° by the sample taken at ωt=90°, signal phase difference module 38 determines information related to θ as follows:

$$\frac{I_{0°}}{I_{90°}} = \frac{-A\sin(\theta)}{A\cos(\theta)} = -\tan(\theta). \quad (4)$$

It should be appreciated the implementation of samples of the signal taken by sampling module 36 at ωt=0°, and at ωt=90° is provided above for illustrative purposes. In other embodiments, in which the samples of the signal are taken by sampling module 36 at predetermined periodic points in the oscillation of the intensity of the electromagnetic radiation emitted by emitter 12 separated by T/4 (e.g., at ωt=180° and at ωt=270°), signal phase difference module 38 determines information related to θ in substantially the same manner as that described above (e.g., by division to determine tan(θ)).

As was mentioned above, in one embodiment, the samples of the signal generated by detector 14 and processed by module 34 is sampled by sampling module 36 at two predetermined periodic points in the oscillation of the intensity of the electromagnetic radiation emitted by emitter 12 that are separated by T/6. For example, the periodic points may include ωt=0°, and at ωt=60°. In this embodiment, the sample taken at ωt=0° can be expressed as shown in equation 2, and the sample taken at ωt=60° may be represented as follows (according to the relationship described in equation (1)):

$$I^{60°} = A\sin(60°-\theta) = -A\sin(\theta-60°) = A\sin\theta\cos 60 - A\cos\theta\sin 60. \quad (5)$$

Signal phase difference module 38 then divides the sample taken at ωt=60° by the sample include ωt=0°, this is represented as follows:

$$\frac{I_{60°}}{I_{0°}} = \frac{A\sin\theta\cos 60 - A\cos\theta\sin 60}{A\sin\theta} = \cos 60 - \sin 60\left(\frac{\cos\theta}{\sin\theta}\right). \quad (6)$$

The relationship expressed in equation (6) can be simplified to the following function, which enables signal phase difference module 38 to determine tan θ as a function of the quotient of the samples taken by sampling module 36:

$$\tan\theta = \frac{\sqrt{3}/2}{\frac{1}{2} - \frac{I_{60°}}{I_{0°}}}. \quad (7)$$

As was the case with respect to the embodiments discussed above in which the predetermined periodic points are separated by T/4, the embodiment in which the predetermined periodic points are ωt=0° and ωt=60° is merely provided for illustration, and other embodiments in which the predetermined periodic points are separated by T/6 are contemplated.

It should be appreciated from the above description that the phase difference θ determined by signal phase difference module 38 is related to the decay of the luminescence of luminescent material 16. If the phase difference θ were an exact measurement of the phase difference between the oscillation of the intensity of the electromagnetic radiation received by luminescent material 16 (e.g., emitted by emitter 12) and the oscillation of the intensity of luminescent radiation 26, then θ would provide an exact measurement of the decay time of the luminescence. In fact, in one embodiment, the phase difference θ determined by signal phase difference module 38 may be implemented as an approximation of the decay time of the luminescence, and information related to the one or more analytes present in the body of gas is determined directly based on θ (e.g., by analyte information module 46, as described below). However, as has been discussed above, various sources of inaccuracy (e.g., detection of radiation by detector 14 other than luminescent radiation 26, delay caused by preliminary processing module 34, etc.) would reduce the accuracy of information determined based on θ without correction (e.g., as discussed below with respect to correction module 44).

1 Amplitude module 40 is configured to determine information related to the amplitude of the oscillation of the intensity of luminescent radiation 26. In one embodiment, this includes determining the amplitude of the oscillation of the output signal(s) generated by photosensitive detector 14 (e.g., as represented by equation (1)) based on the samples of the signal taken by sampling processor 36. As has been discussed above, the samples of the signal taken by sampling processor 36 may include samples taken at predetermined periodic points in the oscillation of the intensity of the electromagnetic radiation emitted by emitter 12 separated by T/4. For example, the predetermined periodic points may include ωt=0°, and at ωt=90°. In this embodiment, amplitude module 40 begins to determine the amplitude of the signal sampled by sampling processor 36 by squaring the samples, and then adding them. These procedures can be represented as follows (based on the relationships described in equations (2) and (3)):

$$I_{0°}^2 + I_{90°}^2 = A^2\sin^2\theta + A^2\cos^2\theta = A^2. \quad (8)$$

As can be seen in equation (8), the amplitude module 40 may then determine the amplitude of the signal sampled by sampling module 36 by determining the square root of the sum of the squares of the samples taken by sampling module 36. In embodiments where the predetermined points at which sampling module 36 samples the signal generated by detector 14 and processed by module 34 are separated by T/6 of the oscillation of the intensity of the electromagnetic radiation emitted by emitter 12 (e.g., ωt=0° and ωt=60°) equations (2) and (5) represent the samples taken. The sample taken at ωt=60° can be further simplified as follows:

$$I_{60°} = \frac{1}{2}I_{0°} + A\sqrt{1-\sin^2\theta}\frac{\sqrt{3}}{2} = \frac{I_{0°}}{2} + \frac{\sqrt{3}}{2}\sqrt{A^2-\sin^2\theta}. \quad (9)$$

This relationship (after further simplification) may be expressed as:

$$2I_{60°} = I_{0°} + \sqrt{3}\sqrt{A^2-I_{0°}^2}, \quad (10)$$

which can be rewritten as the following function that describes the amplitude as a function of $I_{0°}$ and $I_{60°}$:

$$A = \frac{2}{\sqrt{3}}\sqrt{I_{0°}^2 + I_{60°}^2 - I_{0°}I_{60°}}. \quad (11)$$

Amplitude module 40 may implement equation (11) to determine the amplitude of the output signal that is generated by photosensitive detector 14, processed by preliminary processing module 34, and sampled by sampling module 36 at $\omega t=0°$ and $\omega t=60°$.

DC level module 42 is configured to determine a DC level present in an output signal that is generated by photosensitive detector 14, processed by preliminary processing module 34, and sampled by sampling module 36. In one embodiment, such a signal is sampled by sampling module 36 as four predetermined periodic points within the oscillation of the intensity of the electromagnetic radiation emitted by emitter 12 that are separated from each other by T/4 (e.g., $\omega t=0°$, $\omega t=90°$, $\omega t=180°$, and $\omega t=270°$). Theses samples may be represented (according to the relationship described in equation (1)) as follows:

$$I_{0°} = A\sin(0°-\theta)+DC = -A\sin\theta+DC, \quad (12)$$

$$I_{90°} = A\sin(90°-\theta)+DC = A\cos\theta+DC, \quad (13)$$

$$I_{180°} = A\sin(180°-\theta)+DC = A\sin\theta+DC, \text{ and} \quad (14)$$

$$I_{270°} = A\sin(270°-\theta)+DC = -A\cos\theta+DC, \quad (15)$$

A selected two of equations (12)-(15) can then be combined to determine the DC level DC present in the samples. For example, DC can be determined by DC level module 42 using either of the following relationships:

$$DC = \frac{I_0 + I_{180}}{2}, \text{ or} \quad (16)$$

$$DC = \frac{I_{90} + I_{270}}{2}. \quad (17)$$

It should be appreciated that in instances where the signal generated by detector 14 and processed by module 34 includes a DC level, the techniques discussed above with respect to signal phase difference module 38 and/or amplitude module 40 may be adjusted to account for the DC level. For instance, in one embodiment, signal phase difference module 38 implements the samples (taken by sampling module 36) described in equations (12)-(15) to determine the tan $\theta$ as follows:

$$\tan\theta = \frac{2A\sin\theta}{2A\cos\theta} = \frac{I_{180°} - I_{0°}}{I_{90°} - I_{270°}}. \quad (18)$$

In one embodiment, amplitude module 40 implements the samples (taken by sampling module 36) described in equations (12)-(15) as follows:

$$(I_{180°} - I_{0°})^2 + (I_{90°} - I_{270°})^2 = 4A^2(\sin^2\theta + \cos^2\theta) = 4A^2; \therefore \quad (19)$$

$$A = \sqrt{\frac{(I_{180°} - I_{0°})^2 + (I_{90°} - I_{270°})^2}{2}}. \quad (20)$$

Correction module 44 is configured to determine a phase difference between the oscillation of the intensity of the electromagnetic radiation emitted by emitter 12 and the oscillation of the intensity of the luminescent radiation 26 received by photosensitive detector 14. The phase difference can be a corrected phase difference that is determined by applying a correction to the phase difference determined by signal phase difference module 38 (i.e., the phase difference between the oscillation of the intensity of the electromagnetic radiation emitted by emitter 12 and the oscillation of the signal generated by detector 14 and processed by module 34).

In one embodiment, the corrected phase difference is determined based one or more parameters derived from the phase difference determined by signal phase difference module 38. This corrected phase difference may account for one or both of inaccuracies introduced by electromagnetic radiation received by photosensitive detector 14 other than luminescent radiation 26, and a delay caused by processing of processor 34 (e.g., by preliminary processing module 34). Both of these sources of inaccuracy were discussed above. The corrected phasor difference is a function of both (i) the amplitude of the signal that is output by detector 14 and processed by module 34, and (ii) the phase difference determined by signal phase difference module 38. This provides an enhanced correction over systems in which correction applied to a signal phase difference similar to the phase difference determined by signal phase difference module 38 varies with only one of the amplitude of a signal generated by a detector or a magnitude of the determined signal phase difference.

Figure 2A:
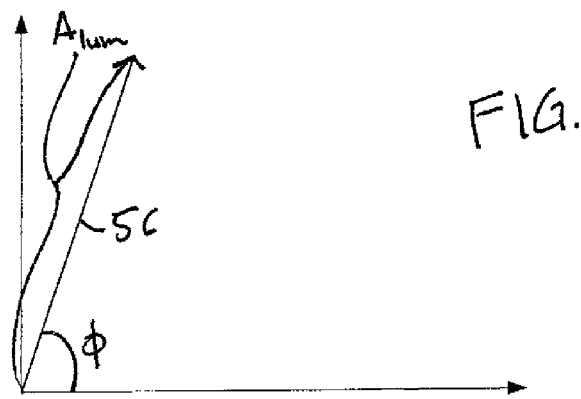
FIGS. 2A-2C illustrate phasor diagrams of output signals generated within a system configured to determine information related to one or more gaseous analytes in a body of gas, according to one embodiment of the invention.
Figure 2B:
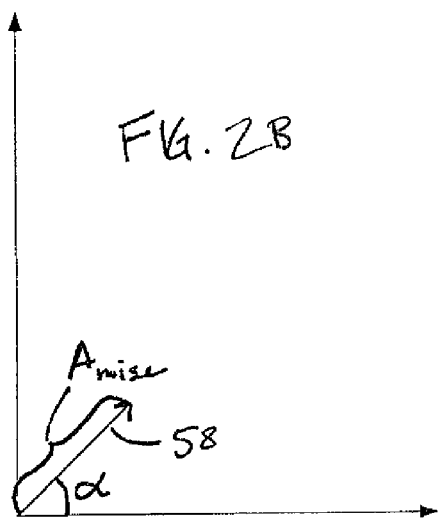
Figure 2C:
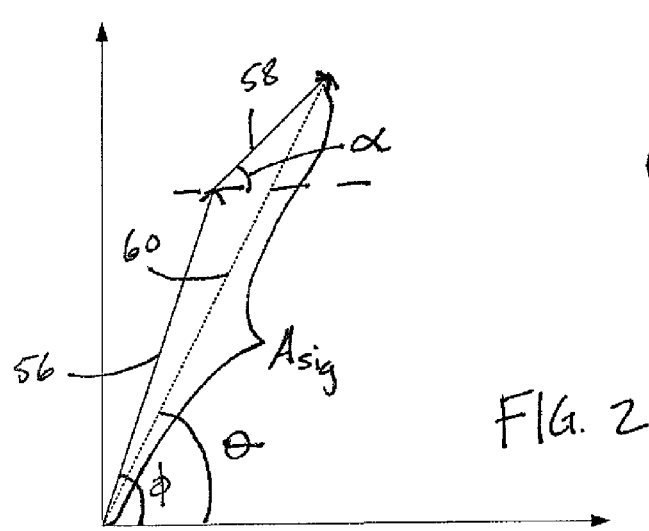

For purposes of illustration, FIGS. 2A-2C are phasor diagrams that illustrates various aspects of the signal generated by detector 14 and processed by module 34. More specifically, FIG. 2A shows a phasor 56 that represents a phase difference $\phi$ (between the signal and the oscillation of the intensity of the electromagnetic radiation emitted by emitter 12) and magnitude of the portion of the output signal generated by detector 14 and processed by module 34 that corresponds substantially to the reception at detector 14 of luminescent radiation 26.

FIG. 2B shows a phase 58 that represents a phase difference $\alpha$ and magnitude of the portion of the output signal generated by detector 14 and processed by module 34 that corresponds to one or more sources of interference in system 10. For example, the one or more sources of noise may include (i) the reception by detector 14 of electromagnetic radiation other than luminescent radiation 26 and/or (ii) the delay (which increases the apparent phase difference of the output signal) caused by the processing of processor 18.

FIG. 2C shows a phasor 60 that represents the phase difference $\theta$ of the signal generated by detector 14 and processed by module 34 that includes both phasor 56 and phasor 58. As can be appreciated from FIGS. 2A, 2B, and 2C, due to the implementation of phasor vectors to determine the appropriate correction for phasor 58, even if the phase difference α and the magnitude of phasor 58 remain constant, the difference between the phase θ and the phase θ that is corrected for by correction module 40 will still vary as the magnitude and phase difference θ of the signal represented by phasor 60 vary.

A derivation of the relationship implemented by correction module 44 to determine the corrected phase difference between the oscillation of the intensity of the electromagnetic radiation emitted by emitter 12 and the oscillation of the intensity of luminescent radiation 26 follows. As is denoted in FIG. 2A, the magnitude of phasor 56 is represented as $A_{lum}$. The X-component of phasor 56 is represented as $X_{lum}$ (which may be rewritten as $A_{lum} \cos \phi$), and the Y-component of phasor 56 is represented as $Y_{lum}$ (which may be rewritten as $A_{lum} \sin \phi$). Similarly, it is denoted in FIG. 2B that the magnitude of phasor 58 is represented as $A_{noise}$. The X-component of phasor 58 is represented as $X_{noise}$ (which may be rewritten as $A_{noise} \cos \alpha$), and the Y-component of phasor 58 is represented as $Y_{noise}$ (which may be rewritten as $A_{noise} \sin \alpha$). Finally, as is denoted in FIG. 2C, for the purposes of the derivation that follows, the magnitude of phasor 60 is represented as $A_{sig}$. The X-component of phasor 60 is represented as $X_{sig}$ (which may be rewritten as $A_{sig} \cos \theta$), and the Y-component of phasor 60 is represented as $Y_{sig}$ (which may be rewritten as $A_{sig} \sin \theta$).

In one embodiment, correction module 44 determines information related to the phase difference φ, such as, tan φ. This can be represented as follows:

$$\tan\phi = \tan(\phi + \alpha - \alpha) \quad (21)$$

$$= \frac{\tan(\theta + \alpha) - \tan\alpha}{1 + \tan(\theta + \alpha)\tan\alpha}$$

$$= \frac{\frac{Y_{sig} - Y_{noise}}{X_{sig} - X_{noise}} - \frac{Y_{noise}}{X_{noise}}}{1 + \frac{(Y_{sig} - Y_{noise})Y_{noise}}{(X_{sig} - X_{noise})X_{noise}}}.$$

Through algebraic expansion and simplification, equation (21) can be rewritten as:

$$\tan\phi = \frac{X_{noise} \cdot Y_{sig} - Y_{noise} \cdot X_{sig}}{X_{sig} \cdot X_{noise} + Y_{noise} \cdot Y_{sig} - (X_{noise}^2 + Y_{noise}^2)}. \quad (22)$$

Since $X_{noise}^2 + Y_{noise}^2 = A_{noise}^2$, equation (22) can be rewritten as:

$$\tan\phi = \frac{X_{noise} \cdot Y_{sig} - Y_{noise} \cdot X_{sig}}{X_{sig} \cdot X_{noise} + Y_{noise} \cdot Y_{sig} - (A_{noise}^2)}. \quad (23)$$

If the top and bottom of the ratio presented in equation (23) are divided by $A_{noise}$, and the relationships $X_{noise} = A_{noise} \cos \alpha$, $Y_{noise} = A_{noise} \sin \alpha$, $X_{sig} = A_{sig} \cos \theta$, and $Y_{sig} = A_{sig} \sin \theta$ are used for substitution purposes, then equation (23) can be rewritten as:

$$\tan\phi = \frac{\cos\alpha \cdot A_{sig}\sin\theta - \sin\alpha \cdot A_{sig}\cos\theta}{\cos\alpha \cdot A_{sig}\cos\theta + \sin\alpha \cdot A_{sig}\sin\theta - A_{noise}}. \quad (24)$$

As was mentioned above, $A_{sig}$ and θ are determined by amplitude module 40 and signal phase difference module 38, respectively. From this information all of the parameters of equation (24) can be determined except for α and $A_{noise}$. In one embodiment, values for α and/or $A_{noise}$ are either stored (e.g., based on a calibration procedure performed by calibration module 48, described further below) or determined (e.g., by delay module 52 as determined below), and thus, may be considered known to correction module 44. Accordingly, correction module 44, in one embodiment, implements the relationship represented in equation (24) to determine the corrected phase difference between the oscillation of the electromagnetic radiation emitted from emitter 12 and the oscillation of luminescent radiation 26 received by photosensitive detector 14.

Referring back to FIG. 1, analyte information module 46 is configured to determine information related to one or more analytes in the body of gas within conduit 22 based on the phase difference between the oscillation of the intensity of the electromagnetic radiation from emitter 12 the oscillation of the intensity of luminescent radiation 26 that is emitted by luminescable medium 16 (e.g., as determined by signal phase difference module 38, as determined by correction module 44, etc.). For example, the phase difference determined by correction module 44 is related to the decay time of the luminescence of luminescable material 16. As was mentioned above, the decay time of luminescable material 16 varies as a function of an amount of one or more gases present at luminescable medium 16. Therefore, analyte information module 46 is able to determine information related to these one or more gases (e.g., an amount present at luminescable material 16) based on the phase difference determined by correction module 44. For example, analyte information module 46 may determine a concentration, a partial pressure, and/or other information related to the one or more gases. In some embodiments, the one or more gases include oxygen.

Calibration module 48 is configured to calibrate system 10 according to a calibration procedure. The calibration procedure enables calibration module 48 to determine values for one or both of α and $A_{noise}$, discussed above with respect to equation (24). This will enable correction module 44 to determine information related to the phase difference between the oscillation of the intensity of the electromagnetic radiation emitted by emitter 12 and luminescent radiation 26 (e.g., according to the relationship expressed in equation (24).

In one embodiment, the calibration procedure includes removing luminescable medium 16 from conduit 22, and then operating system 10 as if luminescable medium 16 were present. This includes emitting electromagnetic radiation from emitter 12 with an oscillating intensity, and receiving radiation to photosensitive detector 14, which generates an output signal in response to the received electromagnetic radiation. It should be appreciated, that since luminescable medium 16 has been removed from conduit 22, the electromagnetic radiation that will reach photosensitive detector 14 during this calibration process will include, substantially exclusively, electromagnetic radiation that would constitute noise (e.g., giving rise to the offset illustrated as phasor 58 in FIG. 2C). Such electromagnetic radiation may include, for example, reflected electromagnetic radiation emitted by emitter 12, and ambient radiation.

It should further be appreciated that the phase difference between oscillation of the intensity of the electromagnetic radiation received by detector 14 during calibration (e.g., reflected radiation) and oscillation of the intensity of the electromagnetic radiation emitted by emitter 12 during calibration should be substantially zero. However, subsequent to processing by preliminary processing module 34 and sampling module 36, signal phase difference module 38 will typically detect a phase difference between oscillation of the output signal generated by detector 14 and oscillation of the intensity of electromagnetic radiation emitted by emitter 12. As has been discussed above, this difference may include a delay introduced by the processing of the output signal by processor 18.

Due to the electromagnetic radiation received by detector 14 during the calibration process, and the delay introduced to the output signal of detector 14 (generated in response to the received electromagnetic radiation) by processor 18, the output signal generated by photosensitive detector 14 may be represented as phasor 58 in FIG. 2B. In order to calibrate system 10, processor 18 processes the output signal generated by photosensitive detector 14 to determine $A_{noise}$ and $\alpha$. For example, signal phase difference module 38 determines $\alpha$ by determining the phase difference between oscillation of the output signal generated by detector 14 during the calibration procedure, and oscillation of the intensity of electromagnetic radiation emitted by emitter 12. Calibration module 48 stores this determination of $\alpha$ for implementation by correction module 44 in the future (e.g., in implementing equation (24)). Similarly, amplitude module 40 determines $A_{noise}$, or the amplitude of oscillation of the output signal generated by photosensitive detector 14 during the calibration procedure, and calibration module 48 stores this determination of $A_{noise}$ for implementation by correction module 44 in the future (e.g., in implementing equation (24)).

In one embodiment, the calibration procedure does not include removing luminescable medium 16 from conduit 22, but instead includes providing one or more analytes with one or more known properties into conduit 22. For example, a known concentration of an analyte (e.g., oxygen) may be included within the body of gas within conduit 22. By way of example, ambient atmosphere may include a known concentration of the analyte (e.g., ~21% oxygen in ambient atmosphere), and ambient atmosphere may be introduced into conduit 22. Then, by leveraging the relationship represented in equation (24), $A_{noise}$ can be determined based on the output signal generated by photosensitive detector 14 while the known concentration of the analyte is present at luminescable medium 16. For example, equation (24) may be rewritten as follows:

$$A_{noise} = A_{sig}\cos\theta \cdot \cos\alpha + A_{sig}\theta \cdot \sin\alpha - \frac{A_{sig}\sin\theta \cdot \cos\alpha - A_{sig}\cos\theta \cdot \sin\alpha}{\tan\phi_{known}}. \quad (25)$$

Because $\tan\phi_{known}$ corresponds to a known phase difference caused by the known concentration of the analyte (the known concentration of oxygen in ambient atmosphere), equation (25) enables calibration module to determine $A_{noise}$ based on the output signal generated by detector 14.

It should be appreciated from equation (25) that the second embodiment of the calibration procedure described above (with the known concentration of the analyte present within conduit 22) does not enable $\alpha$ to be recalculated. Instead, a previously determined value for $\alpha$ is implemented (e.g., determined according to the first embodiment of the calibration procedure described above). Accordingly, in some implementations, calibration module 48 implements the first embodiment of the calibration procedure to determine both $A_{noise}$ and $\alpha$, and then implements the second embodiment of the calibration procedure described above at various intervals to re-determine and/or fine tune the determination of $A_{noise}$. As is discussed below with respect to modules 50, 52, and 54, one or more techniques other than calibration by calibration module 48 may be implemented to monitor and/or fine tune $\alpha$.

As has been mentioned above, in processing the output signal generated by detector 14, processor 18 (e.g., preliminary processing module 34) typically introduces a delay to the signal that may be compensated for within processor 18. In order to determine this delay, simulation module 50 simulates the processing provided to a signal by preliminary processing module 34. For example, simulation module 50 may encode (e.g., from analog to digital, from one digital form to another digital form, etc.) and/or filter (e.g., to provide antialiasing) a signal provided thereto. In one embodiment, the signal provided to simulation module 50 includes the signal generated by driving module 32. In one embodiment, the signal provided to simulation module 50 includes the output signal(s) generated by photosensitive detector 14.

Delay module 52 is configured to determine the delay imparted by simulation module 50 to a signal in simulating at least some of the processing of preliminary processing module 34. In one embodiment, this includes comparing the signal received by simulation module 50 prior to processing with the same signal after being processed by simulation module 50 to determine a delay $\delta$ therebetween.

It should be appreciated that this delay will be substantially the same as the delay introduced into system 10 by the processing of preliminary processing module 34. Because the delay caused by preliminary processing module 34 is the primary component of the phase difference $\alpha$ (illustrated in FIGS. 2B and 2C and discussed above), the delay $\delta$ determined by delay module 52 will drift (e.g., due to variances in temperature, humidity, electronics, etc.) with $\alpha$ in a predetermined relationship. In one embodiment, delay module 52 continuously (or substantially continuously) determines the delay $\delta$ caused by simulation module 50, and delay adjustment module 54 is configured to determine a drift ($\Delta\delta$) from an initial measurement of $\delta$ by delay module 52, or $\delta_0$, where $\delta - \delta_0 = \Delta\delta$. From the determinations of $\Delta\delta$, delay adjustment module 54 determines a corresponding amount by which $\alpha$ should be adjusted ($\Delta\alpha$) to account for the drift $\Delta\delta$. For example, where $\delta$ and $\alpha$ drift in a roughly proportional relationship, $\Delta\alpha$ may be determined by delay adjustment module 54 as $\Delta\delta*k=\Delta\alpha$, where k is a constant of proportionality. In some instances, the correspondence between $\Delta\delta$ and $\Delta\alpha$ may not be precise. In these instances, if $\Delta\delta$ becomes larger than a predetermined amount, delay adjustment module 56 triggers a calibration of system 10 by calibration module 48 that measures $\alpha$ more directly (e.g., the first embodiment of the calibration procedure discussed above).

Figure 3:
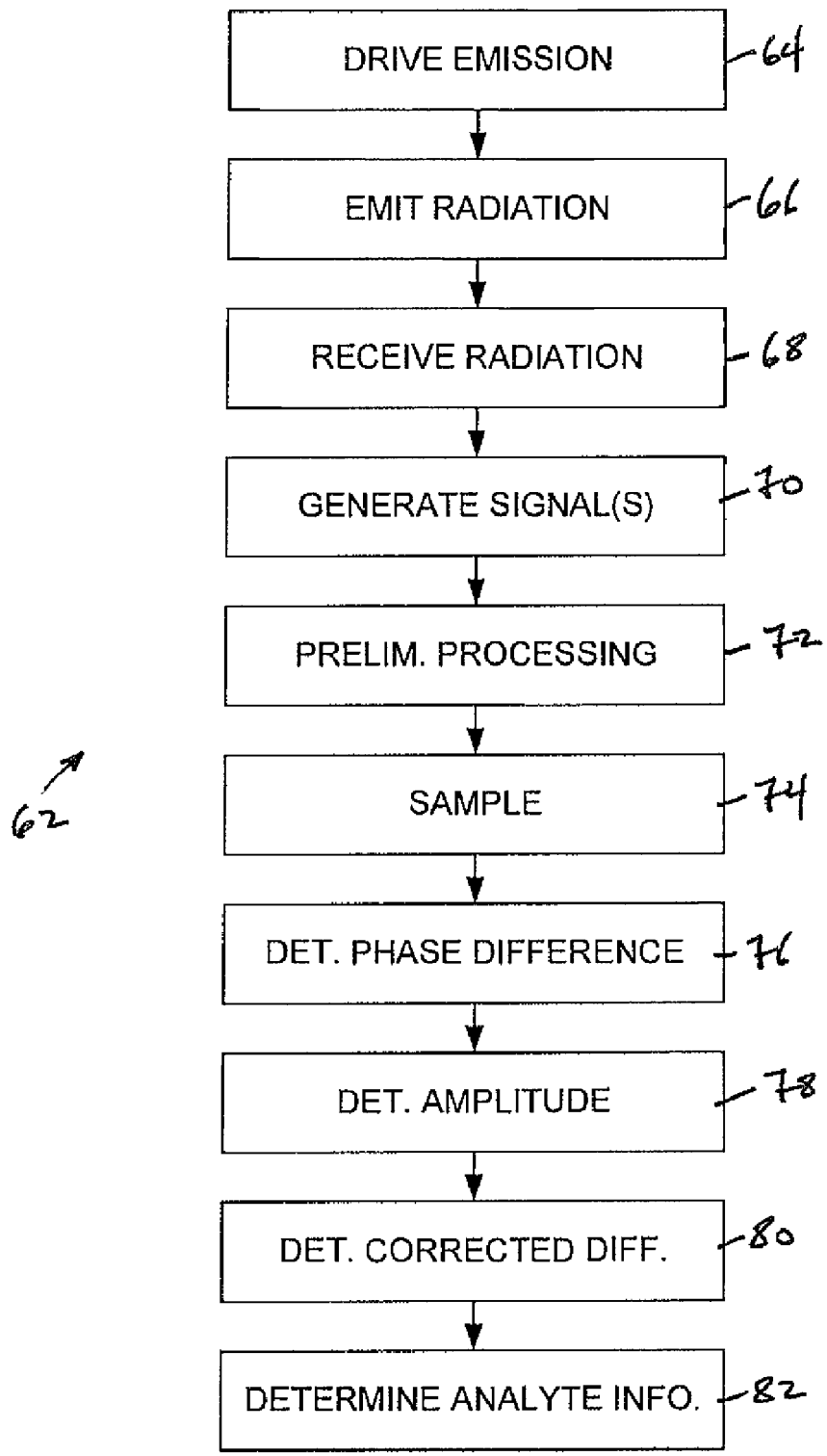
FIG. 3 illustrates a method of determining information related to one or more gaseous analytes in a body of gas.

FIG. 3 illustrates a method 62 of determining information related to one or more gaseous analytes in a body of gas. Although various operations of method 62 are discussed below with respect to components of system 10 (shown in FIG. 1 and described above), it should be appreciated that this is for illustrative purposes only and that such discussion is not intended to be limiting. Instead, method 62 may be implemented in a variety of contexts other than the ones illustrated by system 10.

Method 62 includes an operation 64, at which an emitter is driven to emit electromagnetic radiation with an intensity that oscillates in a periodic manner. Operation 64 may include generating a driving signal to drive the emitter, and/or transmitting the driving signal to the emitter. In one embodiment, operation 64 is performed by a driving module the same as or similar to driving module 32 (shown in FIG. 1 and described above).

At an operation 66, electromagnetic radiation is emitted with an intensity that oscillates in a periodic manner. The intensity of the emitted electromagnetic radiation will oscillate in accordance with a driving signal (e.g., the driving signal generated and/or transmitted in operation 64). Operation 66 further includes emitting the electromagnetic radiation towards a luminescable medium disposed within the body of gas. In one embodiment, operation 66 includes modulating the intensity of electromagnetic radiation emitted from an emitter the same as or similar to emitter 12 (shown in FIG. 1 and described above), and directing the electromagnetic radiation toward a luminescable medium the same as or similar to luminescable medium 16 (shown in FIG. 1 and described above).

At an operation 68, luminescent radiation emitted by the luminescable medium in response to reception of the electromagnetic radiation emitted at operation 66 is received. In one embodiment, the luminescent radiation may be received by a photosensitive detector the same as or similar to photosensitive detector 14 (shown in FIG. 1 and described above).

At an operation 70, one or more output signals that convey information related to the intensity of the luminescent radiation received at operation 68 are generated. In one embodiment, the one or more output signals are generated by the photosensitive detectors implemented to receive the luminescent radiation in operation 68.

At an operation 72, the one or more output signals generated at operation 70 are provide with preliminary processing. The preliminary processing may include, for example, encoding, decoding, filter (e.g., for anti-aliasing, etc.), and/or other processing. In one embodiment, operation 72 is performed by a preliminary processing module of a processor the same as or similar to preliminary processing module 34 of processor 18 (shown in FIG. 1 and described above).

At an operation 74, the one or more output signals are sampled substantially at two or more predetermined periodic points in the oscillation of the intensity of the electromagnetic radiation emitted at operation 66. In on embodiment, operation 74 is performed by a sampling module of a processor the same as or similar to sampling module 36 of processor 18 (shown in FIG. 1 and described above).

At an operation 76, a phase difference between the output signal(s) generated at operation 70 and processed at operation 72, and the oscillation of the intensity of the electromagnetic radiation emitted at operation 66 is determined. The phase difference may be determined based on the samples taken at operation 74. In one embodiment, operation 76 is performed by a signal phase difference module of a processor the same as or similar to signal phase difference module 38 of processor 18 (shown in FIG. 1 and described above).

At an operation 78, an amplitude of oscillation of the one or more output signal generated at operation 70 are determined. The amplitude may be determined based on the samples taken at operation 74. In one embodiment, operation 78 is performed by an amplitude module of a processor the same as or similar to amplitude module 40 of processor 18 (shown in FIG. 1 and described above).

At an operation 80, a corrected phase difference is determined. The corrected phase difference represents the phase difference between the oscillation of the intensity of the electromagnetic radiation emitted at operation 66 and the oscillation of the intensity of the luminescent radiation received at 68. The corrected phase difference is determined based on the phase difference determined at operation 76 and the amplitude determined at operation 78. In one embodiment, operation 80 is performed by a correction module of a processor the same as or similar to correction module 44 of processor 18 (shown in FIG. 1 and described above).

At an operation 82, information related to one or more analytes are determined based on the corrected phase difference determined at operation 80. In one embodiment, operation 82 is performed by an analyte information module of a processor the same as or similar to analyte information module 46 of processor 18 (shown in FIG. 1 and described above).

FIG. 4 illustrates a method 84 of adjusting a determination of a processing delay provided to a signal by a processor. Although various operations of method 84 are discussed below with respect to components of system 10 (shown in FIG. 1 and described above), it should be appreciated that this is for illustrative purposes only and that such discussion is not intended to be limiting. Instead, method 84 may be implemented in a variety of contexts other than the ones illustrated by system 10.

At an operation 86, an oscillating signal is received. In one embodiment, the oscillating signal is the signal actually being processed by the processor. In another embodiment, the oscillating signal is some other oscillating signal.

At an operation 88, one or more processing procedures provided by the processor are simulated with respect to the signal received at operation 86. For example, the one or more processing procedures may include one or more preliminary processing procedures (e.g., encoding, decoding, filtering, etc.) provided by the processor. In one embodiment, operation 88 is performed by a simulation module of the processor the same as or similar to simulation module 50 or processor 18 (shown in FIG. 1 and described above).

At an operation 90, the delay imparted to the signal received at operation 86 by the simulation performed at operation 88 is determined. This delay is related to the processing delay provided by the processor. In one embodiment, operation 90 is performed by a delay module of the processor the same as or similar to delay module 52 of processor 18 (shown in FIG. 1 and described above).

At an operation 92, a drift of the delay determined at operation 90 is determined. The drift of the delay is determined by comparing the drift determined at operation 90 with a previously determined delay. In one embodiment, operation 92 is performed by a delay adjustment module of the processor the same as or similar to delay adjustment module 54 of processor 18 (shown in FIG. 1 and described above).

At an operation 94, the drift of the delay determined at operation 92 is compared with a predetermined threshold. If the drift determined at operation 92 exceeds the predetermined threshold, then method 84 proceeds to a calibration operation 96, at which the delay provided by the processor (as opposed to the delay associated with the simulation performed at operation 88) is calibrated. If the drift determined at operation 92 is determined at operation 94 not to exceed the predetermined threshold, then method 84 proceeds to an operation 98.

At operation 98, an adjustment to a calculation of the delay provided by the processor (as opposed to the delay associated with the simulation performed at operation 88) is determined. The adjustment reflects the drift determined at operation 94. In one embodiment, operation 98 is performed by a delay adjustment module of the processor the same as or similar to delay adjustment module 54 of processor 18 (shown in FIG. 1 and described above).

At an operation 100, the adjustment determined at operation 98 is applied to the calculation of the delay provided by the processor. In one embodiment, operation 98 is performed by a delay adjustment module of the processor the same as or similar to delay adjustment module 54 of processor 18 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it should be understood that the present invention contemplates that, to the extent possible, one or more features of any embodiment can be combined with one or more features of any other embodiment.

What is claimed is:

1. A sensor configured to determine information related to one or more gaseous analytes in a body of fluid, the sensor comprising:
    an emitter configured to emit electromagnetic radiation such that the intensity of the emitted electromagnetic radiation oscillates in a periodic manner;
    a luminescable medium in operative communication with the body of fluid and arranged to receive electromagnetic radiation from the emitter, wherein the luminescable medium emits luminescent radiation in response to the electromagnetic radiation received from the emitter;
    a radiation sensor arranged to receive the luminescent radiation, the radiation sensor generating an output signal that conveys information related to an intensity of the received luminescent radiation; and
    a processor configured to sample the output signal generated by the radiation sensor at two or more predetermined periodic points over the oscillation of the intensity of the electromagnetic radiation emitted by the emitter, and wherein the processor determines information, based on the samples of the output signal, related to a phase difference between the oscillation of the intensity of the electromagnetic radiation emitted by the emitter and oscillation of the intensity of the luminescent radiation received by the radiation sensor,
    wherein the processor is further configured to determine, based on the samples of the output signal, an amplitude of the oscillation of the intensity of the luminescent radiation received by the radiation sensor.

2. A sensor configured to determine information related to one or more gaseous analytes in a body of fluid, the sensor comprising:
    an emitter configured to emit electromagnetic radiation such that the intensity of the emitted electromagnetic radiation oscillates in a periodic manner;
    a luminescable medium in operative communication with the body of fluid and arranged to receive electromagnetic radiation from the emitter, wherein the luminescable medium emits luminescent radiation in response to the electromagnetic radiation received from the emitter;
    a radiation sensor arranged to receive the luminescent radiation, the radiation sensor generating an output signal that conveys information related to an intensity of the received luminescent radiation; and
    a processor configured to sample the output signal generated by the radiation sensor at two or more predetermined periodic points over the oscillation of the intensity of the electromagnetic radiation emitted by the emitter, and wherein the processor determines information, based on the samples of the output signal, related to a phase difference between the oscillation of the intensity of the electromagnetic radiation emitted by the emitter and oscillation of the intensity of the luminescent radiation received by the radiation sensor,
    wherein the periodic points at which the output signal is sampled are separated by a time t, where (a) $t=n*T/4$, or where $t=n*T/6$, where T represents the period of the oscillation of the intensity of the electromagnetic radiation emitted by the emitter, and where n represents an integer.

3. A sensor configured to determine information related to one or more gaseous analytes in a body of fluid, the sensor comprising:
    an emitter configured to emit electromagnetic radiation such that the intensity of the emitted electromagnetic radiation oscillates in a periodic manner;
    a luminescable medium in operative communication with the body of fluid and arranged to receive electromagnetic radiation from the emitter, wherein the luminescable medium emits luminescent radiation in response to the electromagnetic radiation received from the emitter;
    a radiation sensor arranged to receive the luminescent radiation, the radiation sensor generating an output signal that conveys information related to an intensity of the received luminescent radiation; and
    a processor configured to sample the output signal generated by the radiation sensor at two or more predetermined periodic points over the oscillation of the intensity of the electromagnetic radiation emitted by the emitter, and wherein the processor determines information, based on the samples of the output signal, related to a phase difference between the oscillation of the intensity of the electromagnetic radiation emitted by the emitter and oscillation of the intensity of the luminescent radiation received by the radiation sensor,
    wherein the information related to the phase difference between the oscillation of the intensity of the electromagnetic radiation emitted by the emitter and the oscillation of the intensity of the luminescent radiation comprises $\tan(\theta)$, where $\theta$ represents the phase difference.

4. A method of determining information related to one or more gaseous analytes in a body of fluid, the method comprising the acts of:
    emitting electromagnetic radiation having an intensity that oscillates in a periodic manner, wherein the electromagnetic radiation is emitted such that the emitted electromagnetic radiation is incident on a luminescable medium in operative communication with a body of fluid, and wherein the luminescable medium emits luminescent radiation in response to the received electromagnetic radiation;
    receiving at least a portion of the luminescent radiation;
    generating an output signal that conveys information related to the intensity of the received luminescent radiation;
    sampling the output signal at two or more predetermined periodic points over the oscillation of the intensity of the emitted electromagnetic radiation; and
    determining information, based on the samples of the output signal, related to a phase difference between the oscillation of the intensity of the emitted electromagnetic radiation and oscillation of the intensity of the received luminescent radiation, wherein determining information related to the phase difference comprises determining, based on the samples of the output signal, an amplitude of the oscillation of the intensity of the received luminescent radiation.

5. A method of determining information related to one or more gaseous analytes in a body of fluid, the method comprising the acts of:

emitting electromagnetic radiation having an intensity that oscillates in a periodic manner, wherein the electromagnetic radiation is emitted such that the emitted electromagnetic radiation is incident on a luminescable medium in operative communication with a body of fluid, and wherein the luminescable medium emits luminescent radiation in response to the received electromagnetic radiation;

receiving at least a portion of the luminescent radiation;

generating an output signal that conveys information related to the intensity of the received luminescent radiation;

sampling the output signal at two or more predetermined periodic points over the oscillation of the intensity of the emitted electromagnetic radiation; and determining information, based on the samples of the output signal, related to a phase difference between the oscillation of the intensity of the emitted electromagnetic radiation and oscillation of the intensity of the received luminescent radiation, wherein the periodic points at which the output signal is sampled are separated by a time t, where (a) $t=n*T/4$, or (b) where $t=n*T/6$, where T represents the period of the oscillation of the intensity of the emitted electromagnetic radiation, and where n represents an integer.

6. A method of determining information related to one or more gaseous analytes in a body of fluid, the method comprising the acts of:

emitting electromagnetic radiation having an intensity that oscillates in a periodic manner, wherein the electromagnetic radiation is emitted such that the emitted electromagnetic radiation is incident on a luminescable medium in operative communication with a body of fluid, and wherein the luminescable medium emits luminescent radiation in response to the received electromagnetic radiation;

receiving at least a portion of the luminescent radiation;

generating an output signal that conveys information related to the intensity of the received luminescent radiation;

sampling the output signal at two or more predetermined periodic points over the oscillation of the intensity of the emitted electromagnetic radiation; and determining information, based on the samples of the output signal, related to a phase difference between the oscillation of the intensity of the emitted electromagnetic radiation and oscillation of the intensity of the received luminescent radiation, wherein the information related to the phase difference between the oscillation of the intensity of the electromagnetic radiation emitted by the emitter and the oscillation of the intensity of the luminescent radiation comprises $\tan(\theta)$, where $\theta$ represents the phase difference.

* * * * *